United States Patent [19]

Sakurai

[11] Patent Number: 4,654,038

[45] Date of Patent: Mar. 31, 1987

[54] SANITARY NAPKIN

[75] Inventor: Akira Sakurai, Utsunomiya, Japan

[73] Assignee: Kao Corporation, Tokyo, Japan

[21] Appl. No.: 683,743

[22] Filed: Dec. 19, 1984

[30] Foreign Application Priority Data

Dec. 23, 1983 [JP] Japan ............................ 58-198280[U]

[51] Int. Cl.$^4$ ............................................ A61F 13/16
[52] U.S. Cl. ...................................... 604/368; 604/378
[58] Field of Search ............... 604/368, 375, 367, 374, 604/385

[56] References Cited

U.S. PATENT DOCUMENTS

| | | | |
|---|---|---|---|
| 4,269,188 | 5/1981 | Nishizawa et al. | 604/378 |
| 4,333,463 | 6/1982 | Hottman | 604/378 |
| 4,333,464 | 6/1982 | Nakano | 604/368 |
| 4,360,022 | 11/1982 | Usami et al. | 604/368 |
| 4,444,830 | 4/1984 | Erickson | 604/368 |

*Primary Examiner*—John D. Yasko
*Attorney, Agent, or Firm*—Flynn, Thiel, Boutell & Tanis

[57] ABSTRACT

A sanitary napkin composed of a liquid-permeable surface material in contact with the skin, a liquid-impermeable leakproof material and an absorbing member inserted between the surface and leakproof materials, characterized in that said absorbing member is composed of, in the order of contact with the skin, a primary absorbent paper, a mixture of a fluff pulp and a superabsorbent polymer, and a secondary absorbent paper, and that the secondary absorbent paper is covered at least partly with the primary absorbent paper.

7 Claims, 7 Drawing Figures

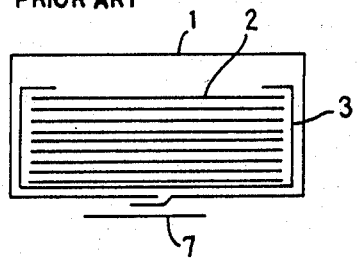
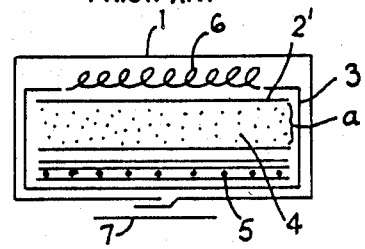
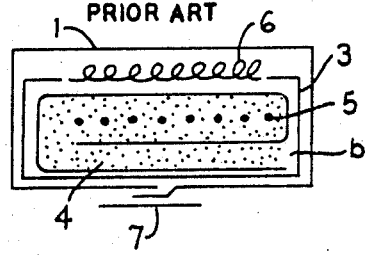
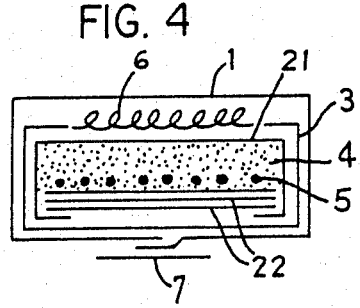
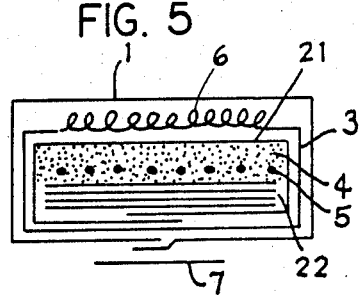
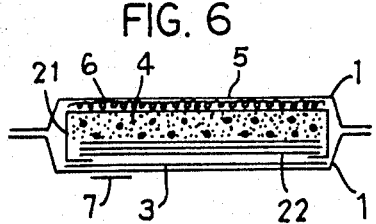
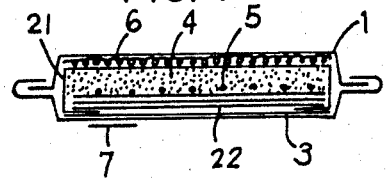

SANITARY NAPKIN

The present device relates to a sanitary napkin for effective absorption of menstrual fluid.

An object of the present device is to provide a sanitary napkin, the morphological stability of which is improved in the manufacturing process, in which the escape of the component materials is prevented, and also which is excellent in absorbency.

BRIEF DESCRIPTION OF THE DRAWINGS

FIGS. 1 to 3 are lateral cross sections of conventional napkins. FIGS. 4 and 5 are lateral cross sections of the napkins of the present device. FIGS. 6 and 7 are longitudinal cross sections of the napkins of the present device. In the drawing, the reference numerals identify elements as listed below 1: Surface material
2, 2', 21, 22: Absorbent paper
3: Leakproof material
4: Fluff pulp
5: Super-absorbent polymer
6: Fluff staple fiber
7: Adhesive tape Sanitary napkins are usually composed of an absorbing member comprising one or both of absorbent paper and cotton-like pulp, that is, fluff pulp, the bottom and the sides of which are covered with a liquid-impermeable leak-proof material, which is further covered entirely with a liquid-permeable surface material, and an adhesive tape provided on the unused surface. An example is illustrated in FIG. 1, in which 1 is a surface material, 2 an absorbent paper, 3 a leakproof material, and 7 an adhesive tape.

Currently super-absorbent polymers, that is, high molecular weight absorbents are often incorporated in the absorbing member for the improvement in absorbency. FIGS. 2 and 3 are examples illustrating the structures of this type of napkin, in which 2' is an absorbent paper laminated on a fluff pulp, 4 a fluff pulp, 5 a super-absorbent polymer and 6 a fluff staple fiber.

The use of super-absorbent polymers, as illustrated in these examples, seems to have improved the absorbency in general, but the following disadvantages are not yet overcome. For example, there are two problems in the structure of the napkin illustrated in FIG. 2: first, as the position of the super-absorbent polymer is close to the unused surface of the napkin, the absorbed menstrual fluid, when in a small amount, can not reach the depth of the super-absorbent polymer 5 but is absorbed by the fluff pulp 4 or the absorbent paper 2', which are conventional component materials. The super-absorbent polymer 5 does not therefore work effectively. Secondly, in the step of laminating the absorbent paper 2' on the fluff pulp 4 to compose a napkin, the pulp or the absorbent paper is sometimes displaced from the position to be laminated, or the fluff pulp sometimes escapes from the terminal part a. These fragments of the fluff pulp may adhere to some part of the processing line, and from there be incorporated in the product, resulting in the contaminating with extraneous matter, which is not desirable from the viewpoint of hygiene.

On the other hand, the napkin illustrated in FIG. 3 is the example having a structure like the letter of an alphabet, "e" in which the both ends of the fluff pulp 4, onto the surface of which the super-absorbent polymer 5 is sprayed, are folded. The discrepancy in the positions of the components of the absorbing member as seen in the napkin of FIG. 2 is sufficiently improved in the napkin of FIG. 3, but the problem of the escape of the fluff pulp is not yet solved because of the presence of part b. The absorbency, on the other hand, is more excellent than that of the napkin of FIG. 2 because the super-absorbent polymer 5, as it is situated near the working surface, is more effectively utilized. Therefore, the napkin of FIG. 3, contrary to that of FIG. 2, shows excellent absorbency when a small amount of menstrual fluid is absorbed. However, when the amount of the fluid to be absorbed is increased, the absence of absorbent paper or other diffusively absorbing material in the structure of the absorbing member increases the amount of the absorbed liquid (menstrual fluid) per unit volume of the absorbing member, resulting in overcharge. This problem may be overcome to some extent by increasing the amount of the super-absorbent polymer or the fluff pulp, but it is not a substantial solution of the problem because an increase in cost and deterioration in applicability due to the thickening of the napkin are caused. The napkin of FIG. 3 is thus disadvantageous in the effective utilization of a napkin in general.

The inventor has arrived at the present device as the result of intensive studies to overcome these disadvantages of the conventional napkins.

Accordingly, the present device provides a sanitary napkin, which substantially extends in the longitudinal direction and is composed of a liquid-permeable surface material in contact with the skin, a liquid-impermeable leakproof material and an absorbing member inserted between said surface and leakproof materials, characterized in that said absorbing member is composed of, in the order of materials nearest the skin, of the user a primary absorbent paper, a mixture of a fluff pulp and a super-absorbent polymer, and a secondary absorbent paper and that said secondary absorbent paper is covered at least partly with said primary absorbent paper.

The sanitary napkin of the present device has the following advantages:

(1) excellent absorbency due to the effective utilization of the entire absorbing member in which a super-absorbent polymer is incorporated, irrespective of the amount of the menstrual fluid to be absorbed, (2) excellent hygienic qualities due to the prevention of the escape of an absorber material, which might otherwise result in the incorporation of extraneous matter in the step of composing a napkin, and (3) low cost.

The present device will now be described in more detail according to the attached drawings.

FIGS. 4 to 7 illustrate examples of the napkin of the present device. FIGS. 4 and 5 are lateral cross sections (in the direction of the minor axis) and FIGS. 6 and 7 are longitudinal cross sections (in the direction of the major axis). The napkin of FIG. 4 is prepared by laminating a fluff pulp 4 on a primary absorbent paper 21 having a somewhat wider breadth than that of the final product, scattering thereon a super-absorbent polymer 5, fixing part or the whole of said super-absorbent polymer 5 in the fluff pulp 4, providing a secondary absorbent paper 22, folding the primary absorbent paper so that it covers the two lateral ends of the secondary absorbent paper 22, thereby forming a covered absorbing member, covering the external surface of said member with a leakproof material 3, further covering the entire napkin with a surface material 1, and providing an adhesive tape 7 on the unused surface.

In the napkin of FIG. 5, the width of the primary absorbent paper 21 is further increased and its lateral ends are allowed to overlap each other so that the secondary absorbent paper 22 is completely covered with the primary absorbent paper 21. Further, in the napkins of FIGS. 6 and 7, the longitudinal ends of the secondary absorbent paper 22 are also covered with the primary absorbent paper 21.

The thus-prepared napkin of the present device is excellent in absorbency and free from leakage or stickiness, due to the rapid contact and effective absorption and retention of even a small amount of menstrual fluid by the super-absorbent polymer 5, which is situated near the working surface, and the effective absorption by an entire napkin, when the amount of the fluid is increased, based on the longitudinal diffusion by the secondary absorbent paper 22 which is provided immediately beneath the super-absorbent polymer 5. Unlike conventional napkins, the entire periphery of the fluff pulp of the napkin of the present device is covered with the primary and secondary absorbent papers 21 and 22. The napkin of the present device is therefore free from incorporation of extraneous matter caused by the escape of the fluff pulp, which has greatly improved hygienic problems. Moreover, as these advantages can be brought about simply by extending to some extent a part of the absorbent paper, which has been used conventionally, the present device is highly advantageous from the viewpoint of cost, because no substantial changes in the structure of the napkin is necessitated. In the practical applications of the present device, there are no limitations in (1) the starting material and process for the preparation of the surface material, (2) use or non-use as well as the starting material and amount of the fluff staple fiber, (3) the amount of the fluff pulp, (4) the type and amount of the superabsorbent polymer, (5) the process for the preparation and amount of the absorbent paper, (6) the type and characteristics of polyethylene-laminated waterproof paper, (7) the type, position, and amount of the adhesive tape, and the like.

The present device will be more readily understood by the following examples, but these examples are not intended to limit the scope of the present device.

EXAMPLE 1

Napkins listed in Table 1 were prepared using the following component materials, and the return amounts, morphology of the products, and the hygienic qualities of the obtained napkins were evaluated. The results are shown in Table 1.

Component materials:
(1) Nonwoven fabric (surface material):
   olefin, heat-bonded
   basis weight: 20 g/m$^2$
(2) Absorbent paper 1:
   100% pulp, a product by an ordinary paper-making process
   basis weight: 18 g/m$^2$
(3) Absorbent paper 2:
   100% pulp, a product by an ordinary paper-making process
   basis weight: 25 g/m$^2$
(4) Leakproof material:
   10$\mu$ polyethylene laminated on 25 g/m$^2$ waterproof paper
(5) Fluff pulp: NBKP type
(6) Super-absorbent polymer: sodium polyacrylate (0.3 g)

Two absorbents, i.e. a rapidly absorbing type (a) and a slowly absorbing type (b) were used.

0.3 g of each of these absorbents (a) and (b) was homogeneously scattering onto a No. 2 filter paper (6 cm in diameter) provided on a support connected to a buret filled with physiological saline, and the cock was opened to start the measurement. The absorption rate of type (a) absorbent was 5 cc/min while that of type (b) absorbent was 2 cc/min.

TABLE 1

| Structure of the napkin | Super-absorbent polymer | Return amount[*1] (g) Small amount absorption | Return amount[*1] (g) Large amount absorption | Morphology and hygienic qualities of the product | |
|---|---|---|---|---|---|
| Products for comparison | | | | | |
| FIG. 1 | — | 1.5 g | 4.2 g | good | |
| FIG. 2 | Type (a) | 1.4 | 2.4 | discrepancy in the absorbent member | Δ |
| FIG. 2 | Type (b) | 1.5 | 2.8 | escape of the pulp | |
| FIG. 3 | Type (a) | 0.8 | 2.0 | no discrepancy | Δ |
| FIG. 3 | Type (b) | 1.1 | 2.6 | escape of the pulp | |
| Products of the present device | | | | | |
| FIG. 4 | Type (a) | 0.7 | 0.9 | no discrepancy | |
| FIG. 4 | Type (b) | 0.9 | 1.2 | no escape | |
| FIG. 5 | Type (a) | 0.8 | 0.8 | no discrepancy | |
| FIG. 5 | Type (b) | 1.0 | 1.2 | no escape | |

(Note)[*1] Return amount

A predetermined amount of physiological saline was rapidly dropped onto the napkin for absorption, and left to stand for 1 minute. 10 sheets of filter paper were placed on the napkin and left to stand for 3 minutes under a load of 50 g/cm$^2$. The filter paper was weighed and the increase in its weight was defined as return amount. 5 g of the physiological saline was dropped for the absorption of a small amount and 10 g for the absorption of a large amount.

As clearly understood from Table 1, the napkin of the present device shows good dryness on the surface, that is, small return amount, in the absorptions of both small and large amounts, and also excellent in the morphological and hygienic qualities of the product. Among the super-absorbent polymers used, the one having a large absorption rate showed better absorbency.

EXAMPLE 2

A napkin was prepared under the same conditions as described in Example 1, except that polyethylene/polypropylene conjugate fiber and rayon were treated by heat-bonding and used as surface material in place of nonwoven fabric, and starch-acrylic acid graft polymer (0.3 g) as super-absorbent polymer, and the absorption characteristics, morphology, and the hygienic qualities of the product were tested in the same manner. The superiority of the product of the present device was shown in every item as in Example 1.

The embodiments of the invention in which an exclusive property or privilege is claimed are defined as follows:

1. A sanitary napkin comprising:
   a longitudinally extending substantially rectangular cubic central absorbent core comprised of a mixture of fluff pulp and super-absorbent polymer;
   a first layer of one or more sheets of absorbent paper disposed immediately below and substantially longitudinally and laterally co-extensive with said central absorbent core;
   a second layer of absorbent paper disposed immediately above and completely covering the upper surface of said central core, said second layer of absorbent paper having edge portions extending downwardly over the longitudinal ends and lateral edges of said central core and extending a predetermined distance under said central core immediately below said first layer of absorbent paper;
   a liquid-impermeable leak-proof material layer substantially enveloping said absorbent paper-covered central core reserving an uncovered portion above said core for passage of fluids from the user to said absorbent layers and central core of the sanitary napkin; and
   a liquid-permeable surface material layer enveloping the entire sanitary napkin.

2. A sanitary napkin as claimed in claim 1, wherein said second layer of absorbent paper extends a distance under said first layer of absorbent paper to form a marginal border therearound.

3. A sanitary napkin as claimed in claim 1, wherein said second layer of absorbent paper extends a distance below said first layer of absorbent paper sufficient to overlap itself and thereby completely envelop said central absorbent core.

4. A sanitary napkin as claimed in claim 1, wherein a layer of fluff staple fiber is disposed above said central core immediately between said surface material layer and said second absorbent paper layer.

5. A sanitary napkin as claimed in claim 4, wherein said second layer of absorbent paper extends a distance under said first layer of absorbent paper to form a marginal border therearound.

6. A sanitary napkin as claimed in claim 4, wherein said second layer of absorbent paper extends a distance below said first layer or absorbent paper sufficient to overlap itself and thereby completely envelop said central absorbent core.

7. A sanitary napkin, comprising:
   an upper, primary, absorbent paper layer;
   an intermediate fluff pulp layer containing particles of super-absorbent polymer mixed therein, the upper surface of said intermediate fluff pulp layer directly underlying and being completely covered by said primary absorbent paper;
   a lower, secondary, absorbent paper layer directly underlying the lower surface of said fluff pulp layer;
   said upper primary absorbent paper layer being of greater width and length than said fluff pulp layer and said secondary absorbent paper layer and having end portions folded so as to cover the lateral ends of said fluff pulp layer and said secondary absorbent paper layer and to underlie at least a portion of the underside of said secondary absorbent paper layer, thereby forming a unitary covered absorbing member in which said fluff pulp layer is completely covered by said primary and secondary absorbent papers, said covered absorbing member consisting essentially of absorbent materials;
   a leakproof film covering the underside and lateral and longitudinal edges of said covered absorbing member;
   and a water-permeable surface material completely enclosing said covered absorbing member and said leakproof film.

* * * * *